United States Patent [19]

Gould et al.

[11] Patent Number: 5,000,955

[45] Date of Patent: Mar. 19, 1991

[54] THERMALLY REVERSIBLE POLYURETHANE HYDROGELS AND COSMETIC, BIOLOGICAL AND MEDICAL USES

[75] Inventors: Francis E. Gould, Princeton; Christian W. Johnston, Neshanic Station; George E. Seems, Pennington, all of N.J.

[73] Assignee: Tyndale Plains-Hunter Ltd., Princeton, N.J.

[21] Appl. No.: 559,513

[22] Filed: Jul. 23, 1990

Related U.S. Application Data

[63] Continuation of Ser. No. 225,906, Jul. 29, 1988, abandoned, which is a continuation-in-part of Ser. No. 920,231, Oct. 17, 1986, abandoned.

[51] Int. Cl.$^5$ .................. A61K 9/00; C08J 3/205; C08L 75/08; C12N 11/08
[52] U.S. Cl. .................. 424/409; 424/60; 424/63; 424/65; 424/69; 424/422; 424/486; 424/78; 514/863; 522/105; 524/591; 524/916; 435/182
[58] Field of Search ............ 524/591, 916; 523/105; 424/409, 422, 486

[56] References Cited

U.S. PATENT DOCUMENTS

| | | | |
|---|---|---|---|
| 3,821,136 | 6/1974 | Hudgin | 521/916 |
| 3,822,238 | 7/1974 | Blair | 528/59 |
| 3,975,350 | 8/1976 | Hudgin | 524/590 |
| 4,155,892 | 5/1974 | Emmons | 524/591 |
| 4,190,566 | 2/1980 | Noll | 524/591 |
| 4,202,880 | 5/1980 | Fildes | 424/78 |
| 4,404,296 | 9/1983 | Schapel | 523/105 |

*Primary Examiner*—C. Warren Ivy
*Attorney, Agent, or Firm*—Ratner & Prestia

[57] ABSTRACT

Thermally reversible polyurethane hydrogels are formed by adding water to a gel forming hydrophilic polyurethane polymer produced by reacting under anhydrous conditions a non-aromatic organic diisocyanate with a glycol component in an NCO/OH mole weight ratio of from about 0.900/1 to about 0.980/1, the glycol component having a number average molecular weight of from about 1000 to 3500 wherein the percentage by weight of the diisocyanate in the reaction mixture is from about 7% to about 20%. The hydrogels are solids at room temperature but liquify at higher temperatures such as body temperature and therefore are useful as carriers for the protection, delivery and sustained release of a variety of active agents including pharmaceuticals, cosmetics, living cells and organisms.

30 Claims, No Drawings

THERMALLY REVERSIBLE POLYURETHANE HYDROGELS AND COSMETIC, BIOLOGICAL AND MEDICAL USES

RELATED APPLICATION

This application is a continuation of application Ser. No. 07/225,906, filed July 29, 1988, now abandoned, which is a continuation-in-part of Ser. No. 06/920,231, filed Oct. 17, 1986, abandoned.

TECHNICAL FIELD

This invention relates to thermally reversible hydrogels and, in particular, to thermally reversible hydrogels produced from certain hydrophilic polyurethane polymers. The invention is also concerned with cosmetic, biological and medical applications of the polyurethane hydrogels such as carrier and delivery systems for active agents, including living cells.

BACKGROUND OF THE INVENTION

U.S. Pat. Nos. 3,822,238 and 3,975,350 describe an active agent carrier system comprising an active agent and as a carrier vehicle therefor, a hydrophilic, preferably cross-linked polyurethane polymer. The carrier system is utilized by subjecting it to aqueous conditions whereby the polyurethane carrier undergoes hydration and swelling with concomitant formation of an insoluble hydrogel from which the active agent is leached out by and into the aqueous medium. The rate and duration of release can be controlled by employing a carrier polymer of the requisite water absorptivity. Generally speaking, polyurethane polymers prepared from water soluble active hydrogen resins, as exemplified by polyoxyethylene polyols, will exhibit the highest water absorptivity. Polymers having diminished water absorptivity can be produced from less soluble resins, or by crosslinking.

The carrier system aforesaid is useful as a means for delivering various active agents, such as medicinal or cosmetic agents, to a treatment zone. For instance, shaped articles made of the carrier system can be inserted into the body to provide precision administering of drugs or serums over extended periods of time.

Another class of hydrophilic polyurethanes that form insoluble hydrogels in the hydrated state is disclosed in U.S. Pat. Nos. 4,156,066 and 4,156,067. These polyurethanes are characterized by the presence of lactone groups in the polymer backbone. The lactone may be opened by hydrolytic cleavage to form carboxylic acid groups which render the polymer soluble in alkaline medium. Other specialized hydrophilic polyurethanes are the polyurethane diacrylates of U.S. Pat. No. 4,359,558 and the polyurethane quaternary ammonium salts of U.S. Pat. No. 4,451,635.

DESCRIPTION OF THE INVENTION

An active agent carrier vehicle utilizing hydrophilic polyurethane polymers has now been discovered which differs in its composition and mode of operation from the polyurethane polymer carrier vehicles heretofore, and the provision of said polyurethane polymer carrier vehicles herein and active agent carrier systems produced therefrom constitute the principal object and purpose of the invention. Other objects and purposes will become manifest in the ensuing description.

The active agent carrier vehicle of the invention is a thermally reversible hydrogel comprising water and a gel-forming, hydrophilic polyurethane polymer which is produced by reacting under anhydrous conditions a non-aromatic, organic diisocyanate with a glycol component comprising a polyoxyethylene glycol or mixture of glycols in an NCO/OH mole weight ratio of from about 0.900/1 to about 0.980/1, the total glycol component having a number average molecular weight of from about 1000 to about 3500. The percentage by weight of the diisocyanate in the anhydrous reaction mixture exclusive of catalyst is from about 7% to about 20%, preferably from about 10% to about 15%.

"Anhydrous" as used in this specification means that the reaction mixture is sufficiently free of water so that the polymer product will be thermally reversible between a gel state and a sol state as further described below. Anhydrous conditions may be produced in any known manner of providing a dry reaction environment. Typical drying procedures include subjecting reactants to heat, vacuum, or contact with dessicating agents. Drying of the glycol component is especially important since glycols commonly contain residual moisture, often in amounts sufficient to deleteriously affect the properties of the herein gel compositions. The dried glycols, which tend to be hygroscopic, should be protected from atmospheric moisture. Other reactants, i.e., isocyanates and catalysts, can ordinarily be used without drying, owing to their lack or near lack of associated moisture. Precautions should also be taken to ensure that all reaction vessels and apparatus are free of moisture.

It is, of course, possible that extremely small or trace amounts of moisture may still be present in the reaction mixture. However, by employing the usual drying techniques such as above described, it has been found that anhydrous conditions suitable for practice of the invention can be realized.

In preparing the thermally reversible hydrogel of the invention, the polyurethane polymer component, preferably granulated or in small pieces, is added to an aqueous medium such as water or an aqueous solution. The resulting mixture is allowed to stand until the polymer undergoes hydration and concomitant swelling. This generally takes about one to four hours, depending on the particular polymer and its state of subdivision.

The aqueous medium containing the swollen polymer is then heated at mildly elevated temperatures with vigorous agitation. Preferably, the heating is conducted at temperatures of from about 37° C. to about 80° C. As a consequence of this treatment, the polymer undergoes a gradual softening. Upon allowing the mixture to cool to room temperature, the polymer is assimilated into the aqueous medium. At this point, heating and stirring are discontinued. By way of analogy to the gel (or hydrogel) and sol states of colloidal dispersions, the resulting liquid may be described as the sol state of the thermally reversible hydrogels of the invention. No necessary limitation to colloidal character is intended, however, since the sol state of the polymer in some respects appears to behave more like a true solution than a colloidal dispersion.

So far as can be ascertained, the assimilation of the polyurethane polymer into the aqueous medium involves both dissolution and dispersion of the polymer. As the temperature of the sol is lowered, it is believed that aggregation of the polymer particles occurs with ensuing reversion to the gel state. But whatever the mechanism of the sol/gel transition, the aqueous polyurethane polymers of the invention constitute a thermally reversible sol/hydrogel-type system.

The temperature at which the sol reverts to the gel and vice versa will depend on the particular polyurethane polymer and its concentration in the aqueous medium. Hydrogels have been obtained after equilibration in which the sol/gel transition occurs in the temperature region of about 30° C. to about 45° C. In general, the concentration by weight of the polymer component in the hydrogel is from about 1% to about 15%, preferably from about 3% to about 7%.

The polyurethane polymer used in forming the thermally reversible hydrogels of the invention is prepared by the reaction of the diisocyanate and glycol component(s) in the presence of a catalyst for the polyurethane reaction. Suitable catalysts include tin compounds such as stannous octoate and organic tin esters as exemplified by dibutyl tin dilaurate, as well as other known catalysts for such reaction. As indicated above, to insure anhydrous conditions the glycol component is freed of moisture prior to reacting it with the diisocyanate. Drying is conveniently effected by heating the glycol component in vacuo (8 mm of Hg or less absolute) at mildly elevated temperatures, typically about 50° C. to about 70° C.

In carrying out the polyurethane reaction, the moisture-free glycol component, diisocyanate and catalyst are brought together at about room temperature or slightly higher but usually not above about 60° C. Where more than one glycol is used, these are preferably formed into a homogeneous mixture or melt before reacting with the diisocyanate. Following mixing of the glycol and diisocyanate components in the presence of the catalyst, a mildly exothermic reaction occurs, the temperature rising to about 50° C. to 80° C. after which the reaction is completed by heating the mixture in the range of about 80° C. to 110° C.

Representative commercial polyoxyethylene glycols are CARBOWAX ® 1450, CARBOWAX ® 4500 and CARBOWAX ® 8000 in which the numbers refers to number average molecular weights. These products are manufactured by Union Carbide Corporation.

The diisocyanates employed in preparing the herein gel forming hydrophilic polyurethanes are of the non-aromatic type. For instance, toluene diisocyanate (TDI) and 4,4'-diphenylmethane diisocyanate (MDI) failed to give a polymer with gel forming properties. Similar negative results were obtained with certain non-aromatic diisocyanates in which both isocyanate functions are attached to a cycloalkane ring. An example of this category of diisocyanates is cyclohexylene diisocyanate.

So far as can be determined, it is believed that suitable diisocyanates for carrying out the invention are characterized by a structure in which the isocyanate groups are connected by an alkylene chain or where each of the isocyanate groups is attached to one of the rings of a dicycloalkane in which the rings are connected via ring carbon atoms by a single chemical bond or through an alkylene chain. A preferred diisocyanate is 4,4'-dicyclohexylmethane diisocyanate, also known as methylenebis (cyclohexyl-4-isocyanate). A less preferred diisocyanate is hexamethylene diisocyanate.

In preparing the polyurethane polymer constituent of the herein hydrogels, the molecular weight (number average molecular weight) of the glycol component, such as polyoxyethylene glycol or mixtures of such glycols, must be such that the stated diisocyanate percentage and NCO/OH mole ratio is preserved in the reaction mixture. Thus, in a polyurethane formulation containing by weight 10% of diisocyanate and 90% glycol and an NCO/OH mole ratio of 1/1, the glycol will have a molecular weight that is about 9 times the molecular weight of the diisocyanate. If the diisocyanate is methylenebis(cyclohexyl-4-isocyanate), which has a molecular weight of 260, then the molecular weight of the glycol will be 9 times 260 or 2340. Glycol molecular weights for other diisocyanate percentages and NCO/OH mole ratios are computed in like manner.

Preferably, the glycol component is a blend of a lower polyoxyethylene glycol (some members of which are sometimes referred to as "alkylene glycols") with a higher member in which the average molecular weight of the glycol blend satisfies the NCO/OH ratio and diisocyanate percentage. Thus, a glycol blend consisting of 1 mole each of CARBOWAX ® 1450 and diethylene glycol M.W. 106.12 would have an average molecular weight of $(1450+106.12)/2$ or 778. Average molecular weights for other mole ratios of glycols are computed similarly. Preferably, the glycol blend will contain an alkylene glycol, such as diethylene, triethylene glycol or a mixture thereof, and one or more higher polyoxyethylene glycols, the average molecular weight of the higher glycols being up to about 10,000, e.g., 4000–10000, to give an average molecular weight of the total glycol component of from about 1000 to about 3500. An especially preferred glycol component is a mixture of about 5% diethylene glycol and about 95% of one or more polyoxyethylene glycols having an average molecular weight in the range of from about 1450 to about 8000.

Generally speaking, high viscosities are encountered when incorporating into the aqueous medium a polyurethane polymer prepared from a polyoxyethylene glycol having a molecular weight approaching 14,000. On the other hand, a polyurethane polymer prepared from a glycol having a molecular weight below about 1450 gives hydrogels that have low viscosities. However, blending the high molecular weight polyoxyethylene glycol with diethylene glycol as above described reduces the viscosity during mixing of the resulting polyurethane polymer with an aqueous medium and produces a satisfactory hydrogel. Blending diethylene glycol with a lower molecular weight polyoxyethylene glycol also produces a satisfactory hydrogel having good gel properties.

The thermally reversible hydrogels of the invention provide a highly effective means for the protection, controlled delivery and sustained release of an active agent. To this end, the hydrogel is melted to the liquid state and the active agent is mixed with the liquid. The temperature of the mixture is then lowered to promote gelling. The active agent is thereby encapsulated in the gel matrix and thus immobilized and protected. On melting the gel, the active material is rendered mobile in the fluidized hydrogel for delivery and application to the treatment area at a rate dependent on its concentration in the gel, the rate at which the gel melts, and other factors such as the environment in which melting occurs. Active agents may also be first dispersed in an aqueous medium used to form the gel state of the polyurethane, thereby being incorporated into the hydrogel during formation thereof.

It can thus be seen that the mechanism whereby the active agent is released from the hydrogel of the invention differs in its mode of operation as compared to leaching of the active agent from the water insoluble, water swellable polyurethane polymers of the cited patents.

Representative active agents, which can be applied singly or in combination by means of the polyurethane hydrogels of the invention, are pharmaceuticals including anti-cancer drugs; agrichemicals including pesticides of all types such as bacteriocides, viricides, insecticides, herbicides, larvacides, fungicides, algaecides and nematocides; topical or dermatological agents such as deodorants, cosmetics, protective screens such as ultraviolet skin coatings, moisturizers and the like; and a host of other substances such as salts, pH regulators, hormones, enzymes and other proteinaceous substances, fragrances, deodorants, humectants, antioxidants, preservatives, and food additives such as flavors, essences and spices.

The hydrogels are also useful as non-toxic culture media for the growth of microorganisms and as gel matrices for the immobilization of enzymes, bacterial cells or other microorganisms in carrying out fermentation reactions such as the manufacture of citric acid. In this specification the term "living cells" is intended to mean and include individual animal and plant cells as well as cell clusters, tissues, organs and organisms including microorganisms such as bacteria, molds and fungi. Furthermore, the hydrogels of the invention can also function as nontoxic media for electrophoretic separation of biological substances such as enzymes, viruses, proteins and nucleic acids in accordance with well known techniques.

In the field of medicine, the hydrogels are useful in a method developed for the treatment of tumors. In this method, the thermally reversible polyurethane in gel form and containing an anti-cancer drug is applied to or at the site of a tumor. The tumor is then subjected to a source of radiant heat such as a diathermy machine. When the temperature of the tumor reaches the point at which the gel becomes fluid, the entrapped drug is released and brought into contact with the tumor. An unexpected and beneficial result is that the combined action of the drug and the heat developed by radiation exert a synergistic effect, thereby enhancing the therapy.

In cosmetic applications, such as in the preparation of face masks, wrinkle creams, mascara bases, dry-skin protectants, and the like, the hydrogels are substituted for or used in addition to the gelatinous substances commonly present in such formulations.

The following non-limiting examples will further illustrate the invention. In the examples, all parts are by weight unless specified otherwise.

EXAMPLE 1

Cell Culturing

A polyether moiety is prepared by mixing 81.4 parts of CARBOWAX ® 4500 polyoxyethylene glycol (Union Carbide Corporation) and 4.1 parts of diethylene glycol with stirring at 70° C. to form a homogeneous melt. The resulting glycol mixture is then subjected to vacuum in order to remove moisture. While continuing the stirring, 14.5 parts of DESMODUR W ® diisocyanate [(methylenebis(cyclohexyl-4-isocyanate), Mobay Chemical Corp.] are added. When the temperature decreases to 50° C., 0.1 part of $T_{12}$ catalyst (dibutyl tin dilaurate, Air Products and Chemicals, Inc.) is added and the mixture allowed to exotherm to about 70° C. The reaction mass is then poured into a polypropylene pan. During pouring, the temperature of the mass continues to rise and, as the temperature approaches 80° C., the mass foams. Upon completion of the pouring operation, the pan is placed in an air circulating oven at 100° C. and maintained in the oven for one hour to cure the polymer.

After cooling to ambient room temperature, the polymer mass is cut into small pieces. A sufficient amount of the small pieces is mixed with water to form a mixture containing 12% solids. The mixture is stirred while increasing the temperature of the mixture to 95° C. With continued stirring, the mass begins to homogenize and then thickens. Upon cooling to 55° C., the mass sets into a highly viscous gel. If desired, lower solids concentration hydrogels may be formed by dilution with water or with an aqueous culture medium. For storage purposes, the hydrogel may be dried.

Hydrogels of any desired solids content and of any desired aqueous consistency may be prepared by mixing the required amount of the dry polymer with water and/or an aqueous medium such as a culture medium, and heating the mixture to about 40° C. with stirring. A hydrogel containing 5% of the above-described polymer with an aqueous culture medium is in its sol state, i.e., a flowable, somewhat syrupy liquid at 37° C. But when cooled to room temperature (20° C.-22° C.), the mixture sets into a solid gel and thus can be used as an agar substitute for the culturing of cells and organisms. The liquid hydrogel may be brought to the desired pH for specific cells or microorganisms (such as $E.\ coli$) by the addition of a buffer solution or a dilute acid or alkaline solution.

EXAMPLE 2

Tumor Treatment

To 81.4 parts of CARBOWAX ® 4500 polyethylene glycol having a number average molecular weight of 4500 is added with mixing 4.1 parts of diethylene glycol. The mixture is heated to 60° C. to 65° C. to form a homogeneous melt which is placed under vacuum until all traces of moisture are removed.

While stirring, 14.5 parts of DESMODUR W ® diisocyanate are added to the mixture. The temperature of the mixture drops. When it reaches about 50° C., 0.2 part of $T_{12}$ catalyst is added. The mixture then starts to exotherm. When the temperature reaches 73° C. to 75° C., the mixture is poured into a polypropylene tray, the tray is placed in a circulating oven and the polymer cured at 100° C. for one hour. The resulting compact slab or polymer is cut into small pieces, using a granulator.

Bleomycin sulfate (an anti-cancer drug) is dissolved in physiological saline at 100 ppm concentration. The granulated polymer is placed in the saline with the drug, 7 parts polymer per 93 parts of the saline, and the polymer allowed to swell for three hours.

After this period, the temperature of the polymer-saline system is slowly raised to 75° C. to 76° C. under vigorous stirring. The polymer dissolves and forms a homogeneous solution. The solution is slowly cooled under constant stirring to 35° C. to 36° C., when the stirring is discontinued and the mixture allowed to gel.

The gel remains solid at temperatures up to 37° C. to 38° C., even in water or physiological saline, and releases the entrapped drug only slowly. When heated to 45° C., the gel melts and releases the entrapped drug rapidly. Thus, it is suitable as a carrier for anti-cancer and other drugs, which can be placed at the tumor site or a site of infection and released during hyperthermia; that is, when the site is overheated to 45° C.

EXAMPLE 3

Cosmetic Uses

In a suitable vessel, 32.0 parts of CARBOWAX ® 1450, 52.7 parts of CARBOWAX ® 8000, and 2.5 parts of diethylene glycol are mixed and heated to 65° C. Vacuum is applied to the heated mixture until all traces of moisture are removed.

To the heated mixture is added 12.7 parts of DESMODUR W ®. When the temperature falls to 45° C. to 48° C., 0.15 part of $T_{12}$ catalyst is added under constant stirring. The mixture starts to exotherm. When the temperature reaches 70° C., stirring is discontinued and the mixture poured into a polypropylene tray. The tray is placed in a circulating oven and the mixture cured for one hour at 100° C.

The solid block of polymer is granulated to $\frac{1}{4}$-inch particles. A gel is prepared therefrom containing 25% solids, following the procedure of Example 1. The solvent in this case is 85 parts of distilled water and 15 parts of SDA ethyl alcohol. The gel has a viscosity of 1,200 cP at 25° C., and is used for preparation of face masks, wrinkle creams and as a base for mascara.

EXAMPLE 4

Skin Protectant

In a suitable vessel, 79.3 parts of CARBOWAX ® 8000 and 5.4 parts of diethylene glycol are melted together at 65° C. and vacuum is applied to remove moisture. 15.3 parts of DESMODUR W ® and 0.2 part of catalyst $T_{12}$ are then added. The mixture exotherms and is poured into a polypropylene tray. The tray is placed in a circulating oven and the mixture cured at 90° C. for 1.5 hours. The resulting polymer is then granulated into $\frac{1}{4}$-inch size pellets.

A gel is prepared from 5 parts of the polymer and 95 parts of water, following the procedure described in Example 1. The gel is easily spreadable on the skin, where it forms an invisible, nongreasy and nontacky film, usable as skin protection for dry skin, psoriasis, etc. The film is easily removed with warm water.

EXAMPLE 5

Polyurethane Gel from Hexamethylene Diisocyanate

Into a suitable vessel was placed 167.98 CARBOWAX ® 8000 and 11.44 g of diethylene glycol. The mixture was warmed to 70° C. to give a homogeneous melt. To this was added 20.58 g of hexamethylene diisocyanate, whereupon the temperature of the resulting mixture dropped to 65° C. After the temperature decreased further to 59° C., 0.4 ml of stannous octoate (T-9) was added. The temperature rose to 90° C. in about 4 minutes and the mixture became viscous. The mixture was then placed in an oven, set at 85° C., for 2 hours. A firm resin was produced.

Gels of the resin were prepared following the procedure given in the previous examples.

We claim:

1. A thermally reversible hydrogel, comprising water and a gel forming hydrophilic polyurethane polymer, produced by reacting under anhydrous conditions an alkylene diisocyanate, bicycloalkane diisocyanate in which the rings are connected via ring carbon atoms by a single bond, or dicycloalkylalkane diisocyanate in which the rings are connected via ring carbon atoms through an alkylene chain, with a glycol component comprising one or more polyoxyethylene glycols, optionally mixed with one or more lower molecular weight ethylene glycols, in a mole weight ratio of NCO/OH of from about 0.900/1 to about 0.980/1, the total glycol component having a number average molecular weight of from about 1000 to about 3500 and wherein the amount by weight of the diisocyanate in the anhydrous reaction mixture is from about 7% to about 20%, mixing the reaction product in an aqueous medium, heating the mixture with stirring until homogeneous, and cooling the mixture.

2. The hydrogel of claim 1 wherein the amount by weight of the diisocyanate is from about 10% to about 15%.

3. The hydrogel of claim 1 wherein the concentration by weight of the polyurethane polymer is from about 1% to about 15%.

4. The hydrogel of claim 1 wherein the concentration of the polyurethane polymer is from about 3% to about 7%.

5. The hydrogel of claim 1 wherein the glycol component is a mixture of a lower molecular weight ethylene glycol and a polyoxyethylene glycol having a number average molecular weight of up to about 10,000.

6. The hydrogel of claim 1 wherein the glycol component is a mixture of diethylene glycol and at least one polyoxyethylene glycol having a number average molecular weight of from about 1450 to about 8000.

7. The hydrogel of claim 1 wherein the diisocyanate is 4,4'-dicyclohexylmethane diisocyanate or hexamethylene diisocyanate.

8. The hydrogel of claim 1 wherein the diisocyanate is 4,4'-dicyclohexylmethane diisocyanate.

9. The hydrogel of claim 6 wherein the glycol component is a mixture of diethylene glycol and a polyoxyethylene glycol having a number average molecular weight of about 1450.

10. The hydrogel of claim 6 wherein the glycol component is a mixture of diethylene glycol and a polyoxyethylene glycol having a number average molecular weight of about 4500.

11. The hydrogel of claim 6 wherein the glycol component is a mixture of diethylene glycol and a polyoxyethylene glycol having a number average molecular weight of about 8000.

12. The hydrogel of claim 6 wherein the glycol component is a mixture of diethylene glycol, a polyoxyethylene glycol having a number average molecular weight of about 1450 and a polyoxyethylene glycol having a number average molecular weight of about 8000.

13. An active agent carrier system comprising an active agent and as the carrier vehicle therefore a hydrophilic, thermally reversible hydrogel comprising water and a gel forming polyurethane polymer produced by reacting under anhydrous conditions an alkylene diisocyanate, bicycloalkane diisocyanate in which the rings are connected via ring carbon atoms by a single bond, or dicycloalkylalkane diisocyanate in which the rings are connected via ring carbon atoms through an alkylene chain, with a glycol component comprising one or more polyoxyethylene glycols, optionally mixed with one or more lower molecular weight ethylene glycols, in a mole weight ratio of NCO/OH of from about 0.900/1 to about 0.980/1, the total glycol component having a number average molecular weight of from about 1000 to about 3500 and the percentage by weight of the diisocyanate in the anhydrous reaction mixture is from about 7% to about 20%, mixing the reaction product in an aqueous medium, heating the mixture with stirring until homogeneous, and cooling the mixture.

14. The carrier system of claim 13 wherein the percentage of the diisocyanate is from about 10% to about 15%.

15. The active agent carrier system of claim 13 wherein the active agent is a pharmaceutical.

16. The active agent carrier system of claim 13 wherein the pharmaceutical is an anti-cancer drug.

17. The active agent carrier system of claim 13 wherein the active agent is a cosmetic agent.

18. The active agent carrier system of claim 17 wherein the cosmetic agent is a fragrance, deodorant or mixture thereof.

19. A skin protectant film produced by applying to the skin the thermally reversible hydrogel of claim 1.

20. A method of delivering an active agent to a treatment zone comprising the steps of:
(1) mixing the active agent with a thermally reversible hydrogel in its liquid state, the said hydrogel comprising water and a hydrophilic polyurethane polymer produced by reacting under anhydrous conditions, an alkylene diisocyanate, bicycloalkane diisocyanate in which the rings are connected via ring carbon atoms by a single bond, or dicycloalkylalkane diisocyanate in which the rings are connected via ring carbon atoms through an alkylene chain, with a glycol component comprising one or more polyoxyethylene glycols, optionally mixed with one or more lower molecular weight ethylene glycols, in a mole weight NCO/OH ratio of from about 0.900/1 to about 0.980/1, the total glycol component having a number average molecular weight of from about 1000 to 3500 and the percentage by weight of the diisocyanate in the anhydrous reaction mixture is from about 10% to about 15%, mixing the reaction product in an aqueous medium, heating the mixture with stirring until homogeneous,
(2) lowering the temperature of the liquid hydrogel to convert it into the solid gel form with concomitant encapsulation therein of the active agent;
(3) introducing the solid hydrogel containing the encapsulated active agent to the treatment zone; and
(4) raising the temperature of the solid hydrogel to convert it to the liquid form, thereby freeing the active agent to exert its therapeutic effect at the treatment zone.

21. The method of claim 20 wherein the hydrogel contains by weight from about 1% to about 15% of the polyurethane polymer.

22. The method of claim 20 wherein the hydrogel contains by weight from about 3% to about 7% of the polyurethane polymer.

23. The method of claim 20 wherein the glycol component is a mixture of a lower molecular weight ethylene glycol and a polyoxyethylene glycol having a number average molecular weight of up to about 10,000.

24. The method of claim 20 wherein the glycol component is a mixture of diethylene and at least one polyoxyethylene glycol having a number average molecular weight of from about 1450 to about 8000.

25. The method of claim 20 wherein the diisocyanate is selected from the class consisting of 4,4'-dicyclohexylmethane diisocyanate and hexamethylene diisocyanate.

26. The method of claim 20 wherein the diisocyanate is 4,4'-dicyclohexylmethane diisocyanate.

27. The method of claim 20 wherein the glycol component is a mixture of a diethylene glycol and a polyoxyethylene glycol having a number average molecular weight of about 1450.

28. The method of claim 20 wherein the glycol component is a mixture of a diethylene glycol and a polyoxyethylene glycol having a number average molecular weight of about 4500.

29. The method of claim 20 wherein the glycol component is a mixture of a diethylene glycol and a polyoxyethylene glycol having a number average molecular weight of about 8000.

30. The method of claim 20 wherein the glycol component is a mixture of diethylene glycol, a polyoxyethylene glycol having a number average molecular weight of about 1450 and a polyoxyethylene glycol having a number average molecular weight of about 8000.

* * * * *